US00PP21828P2

(12) United States Plant Patent
Ui

(10) Patent No.: US PP21,828 P2
(45) Date of Patent: Mar. 29, 2011

(54) ***PETUNIA* PLANT NAMED 'SAKPET001'**

(50) Latin Name: *Petunia hybrida*
Varietal Denomination: SAKPET001

(75) Inventor: Akinobu Ui, Iwata (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/655,959

(22) Filed: Jan. 11, 2010

(51) Int. Cl.
*A01H 5/00* (2006.01)

(52) U.S. Cl. ..... Plt./356

(58) Field of Classification Search ..... Plt./356
See application file for complete search history.

*Primary Examiner*—Annette H Para
(74) *Attorney, Agent, or Firm*—Jondle & Associates, P.C.

(57) ABSTRACT

A *Petunia* cultivar particularly distinguished by a magenta flower with eye and a semi-creeping plant habit, is disclosed.

1 Drawing Sheet

Genus and species: *Petunia hybrida.*
Variety denomination: 'SAKPET001'.

BACKGROUND OF THE NEW PLANT

The present invention comprises a new and distinct cultivar of *Petunia*, botanically known as *Petunia hybrida*, and hereinafter referred to by the cultivar name 'SAKPET001'. It is characterized by having a magenta flower with eye and a semi-creeping plant habit. The new cultivar originated from a hybridization made in Kakegawa, Japan in 2005. The male parent was a proprietary *Petunia* breeding line named '03BCR-14A' (unpatented) and had magenta with white corolla throat flower color and a creeping plant growth habit. The female parent was a proprietary *Petunia* breeding line named '9S-351-3A' (unpatented) and had a red morn flower color and a semi-dwarf plant growth habit.

In June 2005, an F1 generation from the initial hybridization was grown and approximately 500 seeds were obtained. In August 2005, 50 seeds out of the 500 total seeds were sown and 16 plants were cultivated in a greenhouse. Segregation in the F1 generation resulted in plants that had salmon, rose, or magenta flower color and either creeping or semi-creeping plant growth habit. In October 2005, a plant that exhibited magenta with eye-colored flowers and a semi-creeping plant growth habit was selected.

In February 2006, the selection was asexually propagated through plant cuttings in Kakegawa, Japan. Plants of the selection were cultivated and in May 2006, the selected line was observed to have its distinct characteristics remain stable. In July 2006, the selection was asexually propagated again and cultivated. In October 2006, it was confirmed that the line has been shown to reproduce true-to-type in successive generations of asexual propagation. The selection was subsequently named 'SAKPET001'.

DESCRIPTION OF PHOTOGRAPHS

This new *Petunia* plant is illustrated by the accompanying photographs which show the plant form, foliage, and flowers. The colors shown are as true as can be reasonably obtained by conventional photographic procedures.

DESCRIPTION OF THE NEW CULTIVAR

Figure 1:
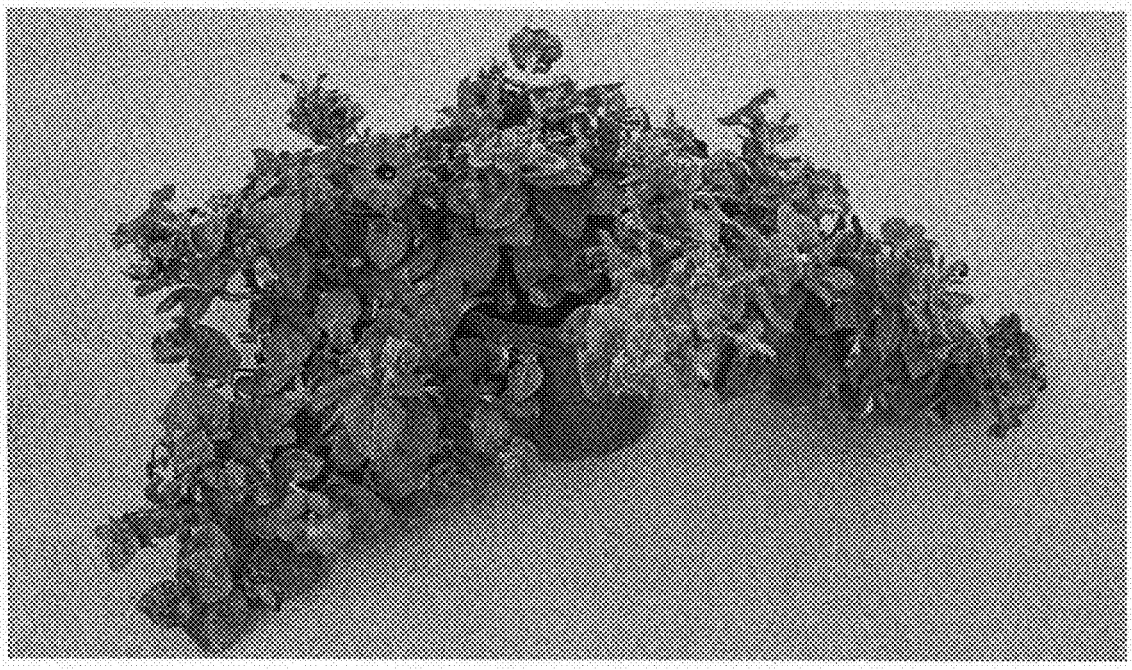
FIG. 1 shows the overall plant habit.
Figure 2:
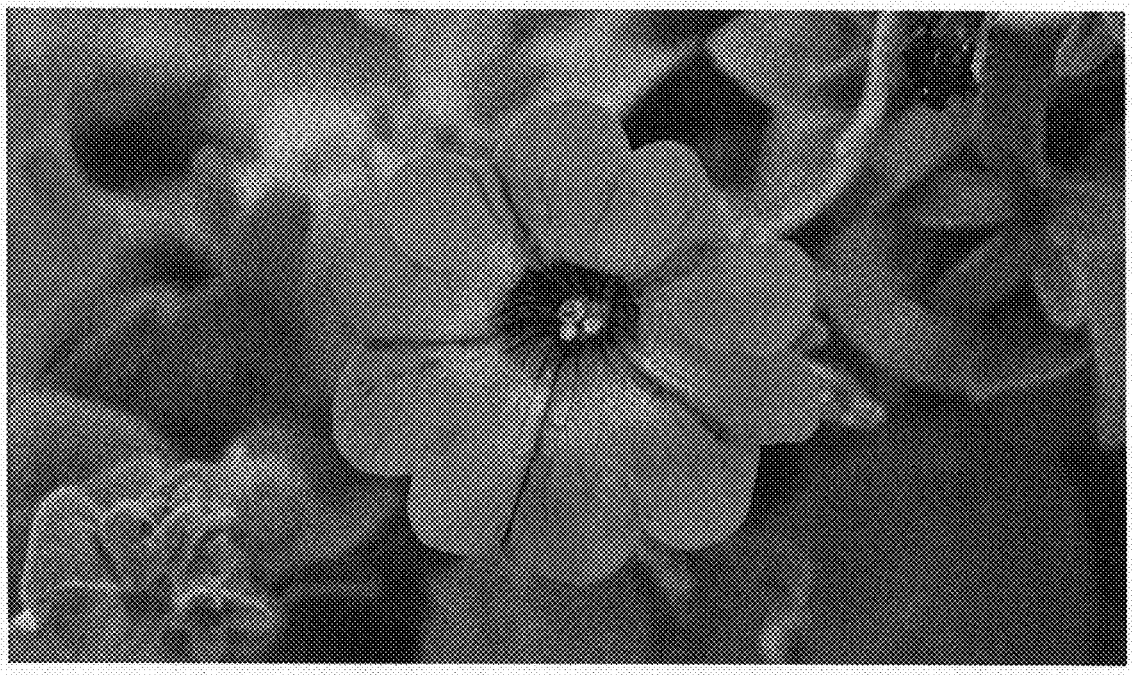
FIG. 2 shows the mature inflorescence.

The following detailed description sets forth the distinctive characteristics of 'SAKPET001'. The data which define these characteristics were collected from asexual reproductions carried out in Salinas, Calif. The detailed description was taken from plants grown under greenhouse conditions for approximately four months from transplanting of rooted cuttings into 6-inch pots. Plants were pinched once during growth. Color references are to The R.H.S. Colour Chart of The Royal Horticultural Society of London (R.H.S.), 4$^{th}$ Edition.

DETAILED BOTANICAL DESCRIPTION

Classification:
- *Family.*—Solanaceae.
- *Species.*—*Petunia hybrida* f. cv. 'SAKPET001'.
- *Common name.*—*Petunia.*

Parentage:
- *Male.*—Proprietary *Petunia* variety named '03BCR-14A' (unpatented).
- *Female.*—Proprietary *Petunia* variety named '9S-351-3A' (unpatented).

Plant description:
- *Life cycle.*—Annual; tender perennial in warm climates.
- *Habit.*—Semi-creeping.
- *Height.*—About 16.0 cm to 17.0 cm from soil line to top of foliage.
- *Spread.*—About 50.0 cm to 52.0 cm.

Propagation:
- *Type cuttings.*—Vegetative cuttings.
- *Time to produce a rooted cutting.*—About 4 weeks.
- *Time to bloom from propagation.*—6 to 8 weeks.

Environmental conditions for plant growth: The terminal 1.0 to 1.5 inches of an actively growing stem was excised. The vegetative cuttings were propagated in five to six weeks. The base of the cuttings were dipped for one to two seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20.0 cm diameter plastic pots in a glass greenhouse located in Salinas, Calif. Pots contained a peat moss-based growing medium. Soluble fertilizer containing 20% nitrogen, 10% phosphorus, and 20% potassium was applied once a day or every other day by overhead irrigation. Pots were top-dressed with a dry, slow release fertilizer containing 20% nitrogen, 10% phosphorus, and 18% potassium. The typical average air temperature was 24° C.

Stems:

*Stem color.*—RHS 144A (Yellow-green).
*Stem diameter.*—About 0.30 cm.
*Stem length.*—About 10.0 cm to 12.0 cm total.
*Stem description.*—Pliable; circular cross-section.
*Stem pubescence.*—Heavy. Stem pubescence color: RHS N155A (White).
*Anthocyanin color.*—RHS N77A (Purple); slight on stems.

Lateral branches:

*Number.*—About 5 main basal branches; many secondary and tertiary branches.
*Length.*—25.0 cm to 30.0 cm.
*Diameter.*—0.50 cm.
*Internode length.*—About 1.0 cm.
*Texture.*—Dull, sticky.
*Color.*—RHS 144A (Yellow-green).

Leaves:

*Leaf arrangement.*—Alternate.
*Leaf shape.*—Elliptical.
*Leaf apex.*—Obtuse.
*Leaf base.*—Attenuate.
*Leaf margin.*—Entire.
*Leaf attachment.*—Petiolate.
*Leaf surface.*—Dull, waxy, and sticky.
*Leaf surface pubescence.*—Slight. Pubescence color: RHS N155A (White).
*Leaf variegation.*—Absent.
*Leaf fragrance.*—Absent.
*Venation.*—Pinnate. Upper surface vein color: RHS 144A (Yellow-green). Lower surface vein color: RHS 144B (Yellow-green).
*Leaf length.*—4.0 cm.
*Leaf width.*—3.0 cm.
*Leaf color.*—Upper surface: RHS 137A (Green) with RHS 144A (Yellow-green) veins. Lower surface: RHS 137B (Green) with RHS 144B (Yellow-green) veins.
*Petiole length.*—About 0.50 cm.
*Petiole diameter.*—About 0.20 cm.
*Petiole color.*—RHS 144B (Yellow-green).

Inflorescence:

*Flowering habit.*—Semi-creeping.
*Number of flowers per node.*—1.
*Flower type.*—Solitary; funnel-shaped with five fused petals.
*Flowering requirements.*—Late Spring to early Fall; will flower with greater than 12 hours of daylight and temperatures above 13° C.
*Duration of flowers.*—Late Spring to early Fall.
*Fragrance.*—Absent.

Bud description:

*Length.*—About 2.5 cm.
*Diameter.*—About 0.80 cm.
*Shape.*—Cylindrical.
*Surface.*—Dull and sticky.
*Pubescence.*—Moderate. Pubescence color: RHS N155A (White).
*Color.*—RHS 79A (Purple) with RHS N77A (Purple) veins.

Corolla:

*Corolla shape.*—Funnel-shaped with 5 fused petals.
*Corolla depth.*—1.0 cm.
*Corolla diameter.*—3.5 cm.
*Corolla tube length.*—2.0 cm.
*Corolla tube diameter.*—3.5 cm.
*Petal shape.*—Obcordate.
*Petal length.*—1.5 cm.
*Petal width.*—1.5 cm.
*Petal apex.*—Acuminate.
*Petal margin.*—Entire.
*Petal pubescence.*—Glabrous.
*Petal color.*—Upper surface: Closest to RHS N79C (Purple) with RHS 79A (Purple) veins. Lower surface: RHS 79D (Purple) with RHS 79A (Purple) veins. Eye zone: RHS 86B (Violet) with RHS 79A (Purple) veins. Corolla tube color: Inner: RHS 86B (Violet) with RHS 79A (Purple) veins. Outer: RHS 86C (Violet) with RHS 79A (Purple) veins. Corolla throat color: RHS 86B (Violet) with RHS 79A (Purple) veins.

Calyx description:

*Arrangement.*—5 sepals; free.
*Length.*—1.5 cm to 2.0 cm.
*Width.*—About 0.20 cm.
*Shape.*—Tubular.
*Apex.*—Obtuse.
*Base.*—Attenuate.
*Margin.*—Entire.
*Attachment.*—Sessile.
*Texture.*—Dull, sticky.
*Color.*—Upper surface: RHS 137B (Green). Lower surface: RHS 144B (Yellow-green).

Peduncle description:

*Length.*—2.0 cm.
*Diameter.*—0.1 cm.
*Texture.*—Sticky.
*Color.*—RHS 144A (Yellow-green).

Reproductive organs:

*Stamen number.*—5; free.
*Stamen form.*—Arranged adjacent to pistil.
*Filament color.*—RHS 77B (Purple).
*Anther length.*—0.20 cm.
*Anther color.*—RHS N92B (Violet-blue).
*Pollen description.*—Powdery; too numerous to count.
*Pollen color.*—RHS 92B (Violet-blue).
*Pistil number.*—1.
*Pistil length.*—0.70 cm.
*Stigma color.*—RHS N82A (Purple-violet).
*Stigma length.*—0.20 cm.
*Style length.*—1.5 cm.
*Style color.*—RHS 144D (Yellow-green).
*Ovary arrangement.*—Superior.
*Ovary surface color.*—RHS 144A (Yellow-green).
*Seed production.*—None observed.

Disease and insect resistance: No unique or distinguishing resistance or susceptibility to common *Petunia* pathogens or pests observed.

Temperature tolerance: No particular temperature tolerances observed.

COMPARISON WITH KNOWN CULTIVARS

'SAKPET001' is a new and distinct cultivar of *Petunia* having magenta flowers with eye and a semi-creeping plant growth habit. 'SAKPET001' is most similar to the commercial *Petunia* variety 'Kakegawa S36' (U.S. Plant Pat. No. 14,037). Table 1 compares some traits of 'SAKPET001' to those of 'Kakegawa S36':

TABLE 1

| Characteristic | 'SAKPET001' | 'Kakegawa S36' |
|---|---|---|
| Petal color, upper surface | Closest to RHS N79C (Purple) with RHS 79A (Purple) veins | RHS N74A (Red-purple) with RHS N78A (Purple) veins |
| Plant growth habit | Semi-creeping | Mounding |

'SAKPET001' is compared with its parental lines in Table 2:

TABLE 2

| Characteristic | 'SAKPET001' | Male Parent: '03BCR-14A' | Female Parent: '9S-351-3A' |
|---|---|---|---|
| Flower color | Magenta with eye | Magenta with white corolla throat | Red morn |
| Growth habit | Semi-creeping | Creeping | Semi-dwarf |

I claim:

1. A new and distinct cultivar of *Petunia* plant as shown and described herein.

* * * * *